(12) United States Patent
Moriyama

(10) Patent No.: US 6,689,052 B2
(45) Date of Patent: Feb. 10, 2004

(54) ENDOSCOPE CHARACTERIZED BY SOFT SECTION THEREOF THROUGH WHICH BUILT-IN COMPONENTS LIE

(75) Inventor: Hiroki Moriyama, Akishima (JP)

(73) Assignee: Olympus Corporation, Tokyo (JP)

( * ) Notice: Subject to any disclaimer, the term of this patent is extended or adjusted under 35 U.S.C. 154(b) by 36 days.

(21) Appl. No.: 09/892,135

(22) Filed: Jun. 26, 2001

(65) Prior Publication Data

US 2002/0002323 A1 Jan. 3, 2002

(30) Foreign Application Priority Data

Jun. 30, 2000 (JP) ........................................ 2000-199740

(51) Int. Cl.[7] ................................................ A61B 1/00
(52) U.S. Cl. ........................ 600/140; 600/139; 600/130; 600/144
(58) Field of Search ................................ 600/139, 140, 600/144, 133, 130

(56) References Cited

U.S. PATENT DOCUMENTS

| | | | | |
|---|---|---|---|---|
| 3,854,473 A | * | 12/1974 | Matsuo | 600/144 |
| 4,329,980 A | * | 5/1982 | Terada | 600/140 |
| 4,977,887 A | * | 12/1990 | Gouda | 600/140 |
| 5,810,715 A | * | 9/1998 | Moriyama | 600/139 |
| 6,179,776 B1 | * | 1/2001 | Adams et al. | 600/121 |

FOREIGN PATENT DOCUMENTS

JP  5-285103  11/1993

* cited by examiner

*Primary Examiner*—John P. Leubecker
(74) *Attorney, Agent, or Firm*—Scully, Scott, Murphy & Presser

(57) ABSTRACT

An endoscope characterized by a soft section thereof through which built-in components lie has a flexible tube and pluralities of metallic built-in components and nonmetallic built-in components. The flexible tube is made by sheathing a metallic tubular member with a nonmetallic tubular member. The pluralities of metallic built-in components and nonmetallic built-in components lie through the flexible tube. As one property of the flexible tube, the hardness of at least a certain portion of the flexible tube, which discourages bending, is determined so that the hardness exhibited by the metallic tubular member that is an integral part of the flexible tube and the metallic built-in components will be higher than the hardness exhibited by the nonmetallic tubular member that is an integral part of the flexible tube and the nonmetallic built-in components.

10 Claims, 3 Drawing Sheets

ENDOSCOPE CHARACTERIZED BY SOFT SECTION THEREOF THROUGH WHICH BUILT-IN COMPONENTS LIE

This application claims benefit of Japanese Application No. 2000-199740 filed in Japan on June 30, the contents of which are incorporated by this reference.

BACKGROUND OF THE INVENTION

1. Field of the Invention

The present invention relates to an endoscope having a plurality of built-in components placed in a soft section thereof that is flexible.

2. Description of the Related Art

Conventionally, endoscopes for medical use are widely used to observe intracavitary organs or to perform various kinds of cures and treatments. The endoscope includes an elongated insertion member that is inserted into a body cavity. Treatment instruments used to perform cures and treatments are, if required, passed through a treatment instrument channel that is formed in the endoscope.

Endoscopes and treatment instruments employed in the medical field are inserted into body cavities for use. When the endoscope or treatment instrument that is used once must be reused to examine or treat another patient, the endoscope or treatment instrument must be cleaned and sterilized at the completion of each examination or treatment in order to prevent inter-patient infection through the endoscope or treatment instrument.

In recent years, autoclaving, that is, so-called high-pressure steam sterilization has become a mainstream of disinfection and sterilization of a medical instrument. This is attributable to the fact that autoclaving is not labor-intensive, enables use of equipment immediately after sterilization, and requires little running costs.

For example, Japanese Unexamined Patent Publication No. 5-285103 has disclosed an endoscopic autoclave that autoclaves an endoscope without affecting the features of the endoscope.

The environment for high-pressure steam sterilization is very severe on an endoscope that is an electronic precision apparatus. For this reason, unlike an endoscope conditioned to undergo ordinary disinfection or sterilization, an endoscope to be sterilized with high-pressure steam is designed to resist high pressure, high temperature, steam, or the like, and is therefore so durable as to withstand severe conditions.

However, even when an endoscope is durable, if the endoscope is repeatedly sterilized with high-pressure steam, a soft section of an insertion member of the endoscope that is inserted into a body cavity is degraded unlike a hard section thereof. The soft section is flexible and resilient and demanded to exhibit a delicate property.

SUMMARY OF THE INVENTION

Accordingly, an object of the present invention is to provide an endoscope whose soft section maintains a delicate property, which it exhibits initially, for a prolonged period of time despite repeated sterilization of the endoscope with high-pressure steam.

Briefly, according to the present invention, there is provided an endoscope characterized by a soft section thereof through which built-in components lie. The endoscope consists mainly of a flexible tube and pluralities of metallic and nonmetallic built-in components. The flexible tube is made by sheathing a metallic tubular member with a nonmetallic tubular member. The pluralities of metallic and nonmetallic built-in components lie through the flexible tube. As one property of the flexible tube, the hardness of at least a portion of the flexible tube which discourages bending is determined so that the hardness exhibited by the metallic tubular member that is an integral part of the flexible tube and the metallic built-in components will be higher than the hardness exhibited by the nonmetallic tubular member that is an integral part of the flexible tube and the nonmetallic built-in components. Consequently, despite repeated sterilization with high-pressure steam, the delicate property of the flexible tube hardly deteriorates.

The above and other objects, features and advantages of the invention will become more apparent from the following description when taken in conjunction with the accompanying drawings.

DESCRIPTION OF THE PREFERRED EMBODIMENTS

Figure 1:
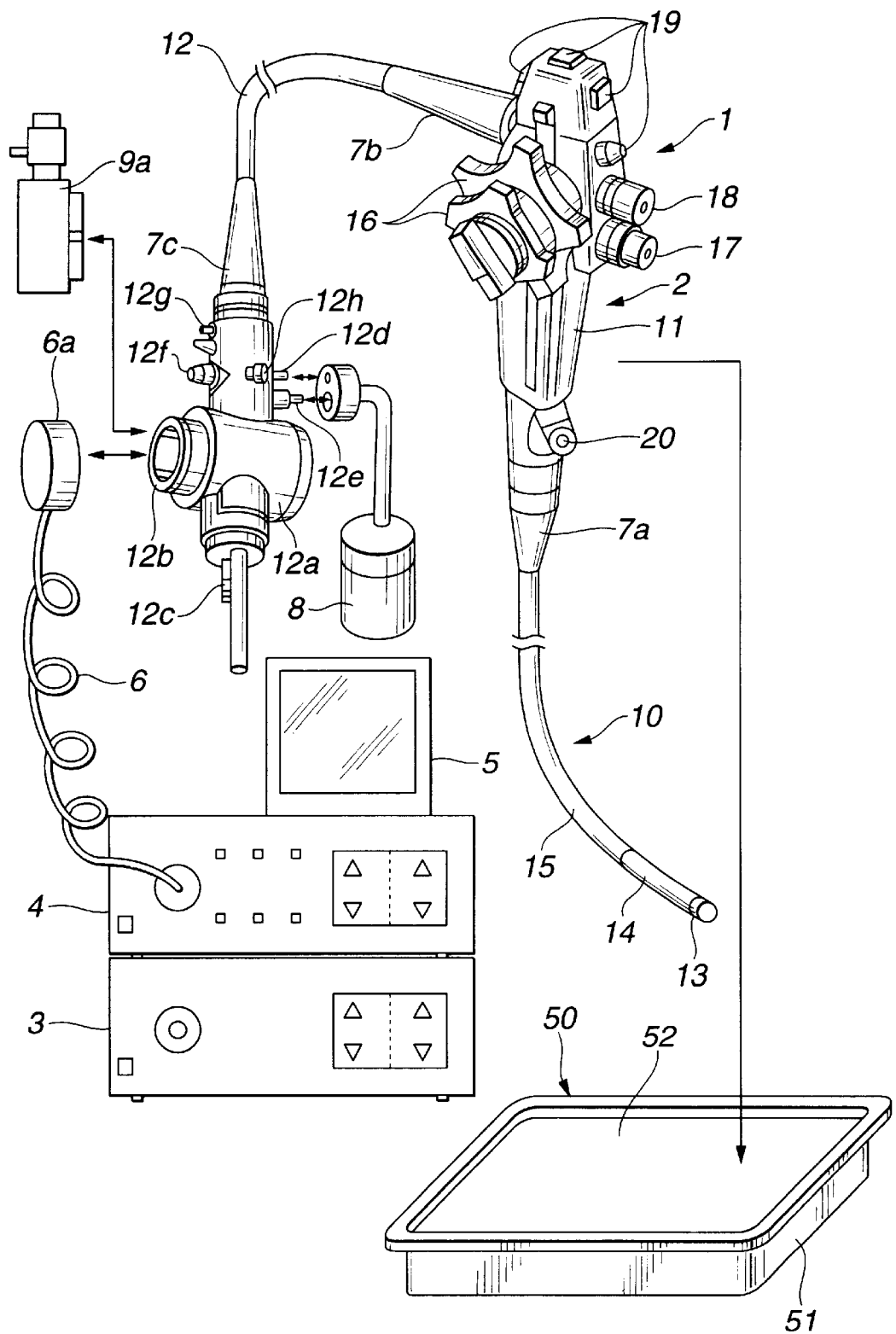
FIG. 1 is an explanatory diagram showing the overall configuration of an endoscope system.

An embodiment of the present invention will be described referring to the drawings below.

A first embodiment of the present invention will be described referring to FIG. 1 to FIG. 4.

Referring to FIG. 1, an endoscope system 1 in accordance with the present invention comprises an electronic endoscope (hereinafter, an endoscope) 2, a light source apparatus 3, a video processor 4, and a monitor 5.

The endoscope 2 has an imaging means. The light source apparatus 3 supplies illumination light to the endoscope 2. The video processor 4 controls the imaging means and processes an image signal generated by the imaging means so as to generate, for example, a video signal. The video processor 4 is connected to the monitor 5. A sterilization case 50 that will be described later accommodates the endoscope 2.

The endoscope 2 comprises an insertion member 10, an operator unit 11, and a universal cord 12. The insertion member 10 is elongated and flexible. The operator unit 11 communicates with the proximal end of the insertion member 10. The universal cord 12 is flexible and extended from the lateral part of the operator unit 11.

A connector 12a that can be attachably and detachably connected or disconnected to/from the light source apparatus 3 freely is attached to an end of the universal cord 12. When the connector 12a is connected to the light source apparatus 3, illumination light emanating from a lamp (not shown) included in the light source apparatus 3 is propagated over a light guide (not shown) lying through the endoscope 2. Thus, a region to be observed is illuminated.

A breakage-of-insertion member preventing member 7a made of an elastic material is adopted as a joint between the insertion member 10 and operator unit 11. The breakage-of-insertion member preventing member 7a is helpful in preventing abrupt bending. A breakage-of-operator unit preventing member 7b made of the same material is adopted as a joint between the operator unit 11 and universal cord 12. A breakage-of-connector preventing member 7c made of the same material is adopted as a joint between the universal cord 12 and connector 12a.

The insertion member 10 of the endoscope 2 is composed of a tip rigid part 13, a bending section 14, and a flexible section 15 that is a soft section. The tip rigid part 13, bending section 14, and flexible section 15 are concatenated in that order from the tip end of the insertion member.

The tip rigid part 13 is made of a hard material. An observation window and an illumination window (not shown) are formed in, for example, the tip surface of the tip rigid part 13. An aeration/perfusion nozzle through which cleaning fluid or air is jetted to the observation window, and a suction port through which humor or filth is sucked is formed at the tip end of the tip rigid part 13.

The bending section 14 has a plurality of bending pieces (not shown) concatenated therein and can therefore be bent freely.

The flexible tube 15 is flexible and resilient and exhibits a delicate property.

The operator unit 11 has an angling knob 16. The angling knob 16 is manipulated properly in order to bend the bending section 14 in a desired direction. By bending the bending section 14, the tip rigid part 13 having the observation window formed therein can be angled in a desired direction.

In addition to the angling knob 16, the operator unit 11 has an aeration/perfusion button 17, a suction button 18, a plurality of remote-control switches 19, and a treatment instrument insertion port 20.

When the aeration/perfusion button 17 is pressed, cleaning fluid or air is jetted out of the aeration/perfusion nozzle. When the suction button 18 is pressed, humor or the like can be sucked through the suction port. The plurality of remote-control switches 19 is used to remotely control the video processor 4. The treatment instrument insertion port 20 opens into a treatment instrument channel tube, which will be described later, lying through the insertion member of the endoscope 2.

An electric connector member 12b is formed on the lateral part of the connector 12a. A signal connector 6a attached to a signal cord 6 extended from the video processor 4 is freely joined to or disjoined from the electric connector member 12b. When the signal connector 6a is plugged in to the endoscope 2, the imaging means incorporated in the endoscope 2 is controlled, and an image signal sent from the imaging means is converted into a video signal. Consequently, an endoscopic view image is displayed on the screen of the monitor 5.

The electric connector member 12b has a vent (not shown) that links the interior and exterior of the endoscope 2. A pressure regulating valve-inclusive waterproof cap (hereinafter a waterproof cap) 9a having a pressure regulating valve (not shown) that blocks the vent is freely mounted on or dismounted from the electric connector member 12b of the endoscope 2.

The connector 12a has an aeration base 12c, a perfusion tank pressurization base 12d, a fluid supply base 12e, a suction base 12f, an injection base 12g, and a ground base 12h.

The aeration base 12c is connected to an aeration source (not shown) incorporated in the light source apparatus 3 so that the aeration base 12c can be connected/disconnected to/from the aeration source freely. The perfusion tank pressurization base 12d and liquid supply base 12e are connected to a perfusion tank 8 that serves as a liquid supply source so that they can be freely connected/disconnected to/from the perfusion tank 8. The suction base 12f is connected to a suction source (not shown) used to perform suction through the suction port. The injection base 12g is connected to a perfusion unit (is not shown) used to perform perfusion. An electric cable is coupled to the ground base 12h. Consequently, high-frequency leakage current arisen during high-frequency treatment is fed back to a high-frequency treatment unit (not shown).

After used to observe or treat a lesion, the endoscope 2 can be cleaned or sterilized with high-pressure steam. Before the endoscope 2 is sterilized with high-pressure steam, the waterproof cap 9a is joined to the electric connector member 12b. Before the endoscope 2 is sterilized with high-pressure steam, the endoscope 2 is placed in the sterilization case 50.

The sterilization case 50 is composed of a tray 51 that is a case body and a lid member 52. The tray 51 has a restriction member (not shown) molded in line with the shape of an endoscope so that the insertion member 10, operator unit 11, universal cord 12, connector 12a, and other components of the endoscope 2 can be settled at predetermined positions. The tray 51 and lid member 52 each have many pores, through which high-pressure steam is introduced into the case, bored therein.

A porous composite film that does not pass water but passes steam may be laid down in the tray 51, whereby cleaning fluid can be reserved in the tray 51. The composite film resists the cleaning fluid. Therefore, the tray 51 can be used to clean the endoscope 2. After the endoscope is cleaned, the endoscope 2 is settled at the predetermined position in the tray 51. The sterilization case 50 is then placed in a high-pressure steam sterilization apparatus in order to sterilize the endoscope.

Figure 2:
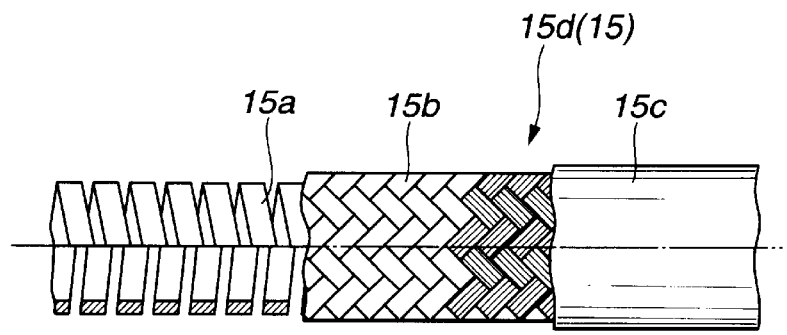
FIG. 2 is an explanatory diagram showing the appearances of members constituting an armor.
Figure 3:
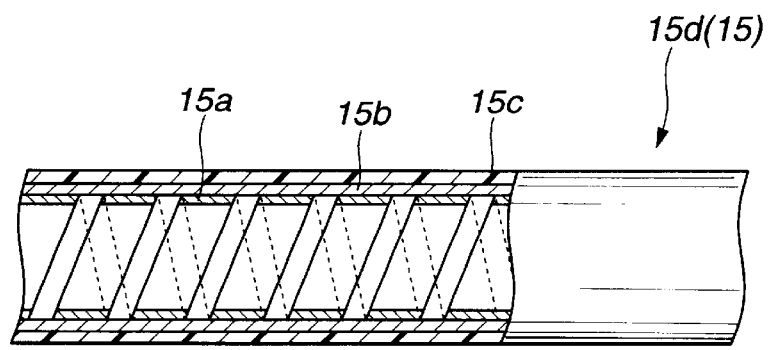
FIG. 3 is a sectional view showing the structure of the armor.

Referring to FIG. 2 and FIG. 3, the flexible tube 15 is formed with an armor 15d made by layering a spiral tube 15a, a braid 15b, and a sheathing tube 15c in that order from the innermost layer. The flexible tube 15 that is the armor 15d has the tip part thereof coupled to the proximal part of the bending section 14, and has the proximal part thereof coupled to the tip part of the operator unit 11.

The spiral tube 15a is a tubular member made by spirally winding a metallic strip that is a thin belt-like metallic member. The braid 15b is a tubular member made by plaiting metallic or nonmetallic strands. The sheathing tube 15c is a tubular member that is made of a resin material and is a nonmetallic member.

The sheathing tube 15c is made of, for example, an ester-series thermoplastic elastomer, an amide-series thermoplastic elastomer, a styrene resin, a fluorocarbon rubber, a silicon rubber, or the like. Moreover, the universal cord 12 has substantially the same structure as the flexible tube 15. Incidentally, the spiral tube 15a may be made by doubling or tripling a plurality of belt-like metallic strips.

Figure 4:
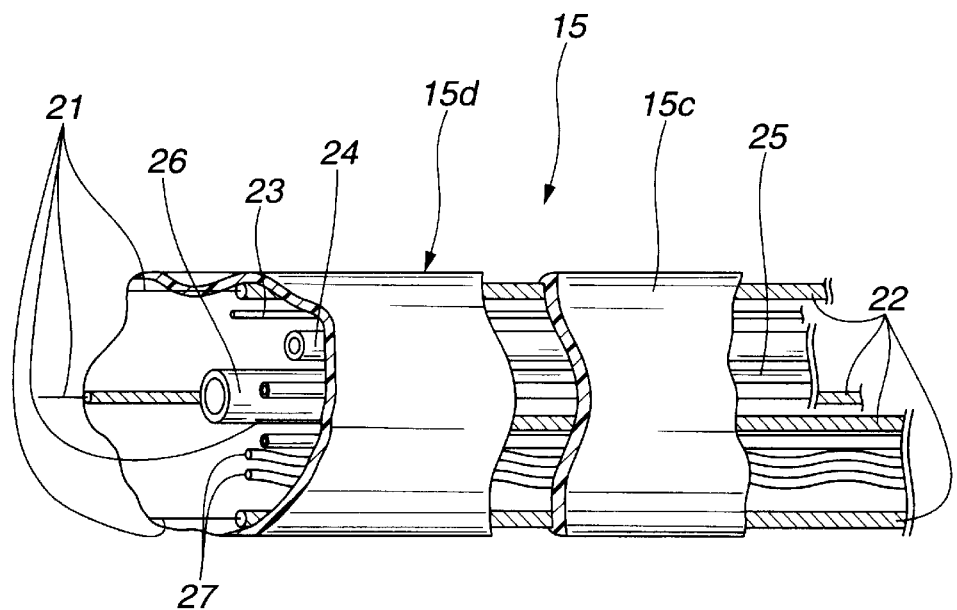
FIG. 4 is an explanatory diagram showing built-in components placed in a soft section.

As shown in FIG. 4, various built-in components lie through the flexible tube 15 of the endoscope 2.

The built-in components include metallic built-in components that are metallic members, and nonmetallic built-in components that are nonmetallic members. What are referred to as the metallic members are metallic members made of stainless steel, aluminum, or a super-elastic alloy.

Specifically, the metallic built-in components include angulation wires 21, wire sheathing coils 22, and a stylet 23. The angulation wires 21 are advanced or withdrawn responsively to a manipulation performed on the angling knob 16, whereby the bending section 14 is bent. The wire sheathing coils 22 sheath the angulation wires 21 while being loosely engaged with it. The stylet 23 is a flexibility adjustment metallic member that will be described later.

On the other hand, the nonmetallic built-in components include the perfusion tube 24 that is a tube made of a resin, an aeration tube 25, a treatment instrument channel tube 26, and a signal cable 27 that is composed of a resin sheath and a metallic wire.

A description will be made of typical conditions under which high-pressure steam sterilization should be performed.

The conditions are stipulated in the standards ANSI/AAMI ST37-1992 recommended by the American National Standards Institute (ANSI) and published from the Association for the Advancement of Medical Instrumentation (AAMI). Namely, a pre-vacuum sterilization process requires that sterilization be performed at 132° C. for four minutes, while a gravity sterilization process requires that sterilization be performed at 132° C. for ten minutes.

The condition of temperature for high-pressure steam sterilization varies depending on the type of a high-pressure steam sterilization apparatus or the sterilization time required by a sterilization process. In general, the temperature ranges from about 115° C. to about 138° C. However, some types of sterilization apparatuses permit about 142°.

The sterilization time varies depending on the sterilization temperature required by a sterilization process. In general, the sterilization time ranges from about three minutes to about sixty minutes. Some types of sterilization apparatuses permit about one hundred minutes.

The pressure in a sterilization chamber is generally set to +0.2 MPa with respect to the atmospheric pressure.

Next, a typical pre-vacuum process for sterilizing the endoscope 2 with high-pressure steam will be described briefly.

At first, the waterproof cap 9a is joined to the electric connector member 12b of the endoscope 2 that is an object of sterilization. Thereafter, the endoscope 2 is placed in the sterilization case 50, and the sterilization case 50 is installed in a sterilization chamber (not shown). Prior to high-pressure sterilization, the sterilization chamber is decompressed (this step may be referred to as a pre-vacuum step).

Since the waterproof cap 9a is joined to the electric connector member 12b, the pressure regulating valve is closed to block the vent. In other words, the interior of the endoscope 2 is kept watertight while being shielded from the exterior thereof.

The pre-vacuum step is needed to infiltrate steam into the details of the object of sterilization at a sterilization step. At this step, since the sterilization chamber is decompressed, high-pressure high-temperature steam permeates the object of sterilization. At the pre-vacuum step, the pressure in the sterilization chamber is set to range from −0.07 MPa to −0.09 MPa with respect to the atmospheric pressure.

When the pressure in the sterilization chamber is released at the pre-vacuum step, the external pressure of the endoscope 2 becomes lower than the internal pressure thereof, or in other words, there arises a difference between the internal and external pressures of the endoscope 2. This causes the pressure regulating valve of the waterproof cap 9a to open.

The interior of the endoscope 2 communicates with the exterior thereof through the vent. Consequently, the difference in pressure between the interior and exterior of the endoscope 2 is prevented from increasing. Namely, the endoscope 2 is protected from being broken due to the difference in pressure.

Thereafter, a description will be made of a sterilization step of feeding high-pressure high-temperature steam into the sterilization chamber so as to sterilize the endoscope.

At the sterilization step, the sterilization chamber is pressurized. Consequently, the external pressure of the endoscope 2 becomes higher than the internal pressure thereof, or in other words, there arises a difference in pressure between the interior and exterior of the endoscope 2. This causes the pressure regulating valve of the waterproof cap 9a to close. Eventually, high-pressure steam is prevented from invading into the interior of the endoscope through the vent.

Nevertheless, high-pressure steam gradually invades into the interior of the endoscope while penetrating through the sheathing tube 15c of the flexible tube 15 made of a high polymer material or an O ring (not shown) made of a fluorocarbon rubber or a silicon rubber. The O ring is a sealing means attached to joints in the endoscope 2.

At this time, in the endoscope 2, pressure released at the pre-vacuum step and pressure applied at the sterilization step are added up. In other words, pressure is applied from the exterior of the endoscope to the interior thereof.

Then, after the sterilization step is completed, the sterilization chamber is decompressed again in order to dry the sterilized object of sterilization (dry step).

At the dry step, the sterilization chamber is decompressed in order to remove steam from the sterilization chamber. This facilitates drying of the endoscope 2. At the dry step, the pressure in the sterilization chamber is generally set to range from −0.07 MPa to −0.09 MPa with respect to the atmospheric pressure. The dry step is performed arbitrarily if required.

At the dry step succeeding the sterilization step, the pressure in the sterilization chamber is released. Consequently, the external pressure of the endoscope 2 becomes lower than the internal pressure thereof, or in other words, there arises a difference between the internal and external pressures of the endoscope 2. Substantially at the same time when the difference between the internal and external pressures arises, the pressure regulating valve of the waterproof cap 9a opens, and the interior and exterior of the endoscope 2 communicates with each other through the vent. Thus, the difference in pressure between the interior and exterior of the endoscope is prevented from increasing.

After the decompression step is completed, the sterilization chamber is pressurized. When the external pressure of the endoscope 2 becomes higher than the internal pressure thereof, or in other words, there arises a difference in pressure between the interior and exterior of the endoscope, the pressure regulating valve of the waterproof cap 9a closes.

When the high-pressure steam sterilization process is completed, pressure equivalent to pressure released at the decompression step is applied externally to the housing of the endoscope 2. When the waterproof cap 9a is disjoined from the electric connector member 12b, the interior and exterior of the endoscope 2 communicates with each other through the vent. Consequently, the internal pressure of the endoscope 2 becomes equal to the atmospheric pressure. Eventually, the housing of the endoscope 2 is relieved from a load stemming from the difference in pressure.

As mentioned above, during sterilization, the interior and exterior of the flexible tube 15 of the endoscope 2 are exposed to high-pressure steam. Therefore, if the endoscope 2 having the flexible tube 15 is repeatedly sterilized with high-pressure steam, although the properties of the metallic members relatively are unsusceptible to high-pressure steam, the properties of the nonmetallic members or especially the resin members deteriorate gradually.

In other words, the properties of the flexible tube 15, that is, the flexibility and resiliency thereof that are essential in inserting the insertion member 10 into a patient's body cavity may deteriorate because of repeated sterilization with high-pressure steam. Namely, the flexible tube 15 may be gradually softened, or on the contrary, hardened. When the properties of a resin member deteriorate, the properties of the flexible tube 15, that is, the flexibility and resiliency thereof change. This leads to a change in inserting smoothness.

If the flexible tube 15 is hardened, the diameter of a circle traced by the bent flexible tube becomes larger. This leads to deterioration of inserting smoothness. Moreover, when resiliency deteriorates, the property of recovering quickly from a bent state is impaired. This results in deterioration of inserting smoothness.

In consideration of the above drawbacks, according to the present embodiment, the flexible tube 15 of the endoscope 2 is designed to exhibit a predetermined property for fear the foregoing properties of the flexible tube 15 may change largely. The predetermined property is exhibited based on the relationships in hardness among the members constituting the armor 15*d* that is the flexible tube 15, and the relationships in hardness among the built-in components lying through the flexible tube 15.

Specifically, when the flexible tube 15 is designed to exhibit the predetermined property, the members constituting the armor 15*d* that is the flexible tube 15 and the built-in components lying through the flexible tube are divided into metallic members and nonmetallic members. Within a predetermined range that is an arbitrary portion of the flexible tube 15, the sum of the hardness levels of the metallic members whose properties are unsusceptible to high-pressure steam is made larger than the sum of the hardness levels of the nonmetallic members whose properties are susceptible to high-pressure steam.

Herein, the metallic members of the flexible tube 15 include the spiral tube 15*a* that is an integral part of the armor 15*d*, and the angulation wires 21, wire sheathing coils 22, and stylet 23 which are built-in components. In contrast, the nonmetallic members of the flexible tube 15 include the braid 15*b* and sheathing tube 15*c* that are integral parts of the armor 15*d*, and the perfusion tube 24, aeration tube 25, treatment instrument channel tube 26, and signal cable 27 that are built-in components.

The stylet 23 is made of a super-elastic alloy and included for optimizing the flexibility (or hardness) of the flexible tube 15. The stylet 23 is a flexibility adjustment metallic member. The stylet is used to attain excellent resiliency and make the flexible tube 15 durable enough to withstand bending repeated at a small curvature.

The diameter of the stylet 23 ranges from about $\phi 0.5$ mm to about $\phi 1.5$ mm. The stylet 23 can therefore be placed in a space left unoccupied by the other built-in components. According to the present embodiment, one or more stylets 23 are placed at predetermined positions along the spiral tube 15*a* in the longitudinal direction of the flexible tube 15 in order to attain desired flexibility.

The stylet 23 has nothing to do with aeration, perfusion, suction, conduction, or the like and does not react directly on a patient's mucosa. The stylet 23 is intended mainly to provide the flexible tube 15 with desired flexibility and resiliency. The stylet 23 is therefore not extended up to the tip rigid part 13 and does not affect the smoothness in bending the bending section 14.

Moreover, the braid 15*b* that is an integral part of the flexible tube 15 may be metallic or nonmetallic. Even if the braid 15*b* is made of a metal, the braid 15*b* is brought into close contact with the sheathing tube 15*c*. The braid 15*b* is therefore, similarly to the sheathing tube 15*c*, a nonmetallic member.

Furthermore, the signal cable 27 is usually composed of a resin sheath and a metallic wire. The signal cable 27 is also a nonmetallic member.

Now, a description will be made of an example of a way of checking the hardness exhibited by the metallic members and that exhibited by the nonmetallic members.

The endoscope 2 having the components thereof assembled and exhibiting desired flexibility is made available. The hardness exhibited by a predetermined range of the flexible tube 15 of the endoscope 2 is measured.

Thereafter, the hardness exhibited by the metallic members of the flexible tube 15 is measured. The angulation wires 21, wire sheathing coils 22, and stylet 23 that are the metallic hard members of the flexible tube 15 of the endoscope 2 and supposed to lie in the same portion of the flexible tube 15 are placed in the flexible tube 15, and the hardness exhibited by these metallic members is measured. It is then checked if the measured hardness exceeds 50% of the hardness of the flexible tube 15.

If the hardness exhibited by the metallic members exceeds 50% of the hardness of the flexible tube 15, it means that the sum of the hardness levels of the metallic members lying in the predetermined range is larger than the sum of the hardness levels of the nonmetallic members.

According to the present embodiment, a magnitude of force required to bend a member by a predetermined angle is, for convenience' sake, referred to as a hardness level. As far as the flexible tube 15 is concerned, a magnitude of force required to bend a certain portion of the flexible tube 15 until the portion traces an arc of, for example, 20 cm in diameter is referred to as the hardness level of the flexible tube 15. Bending the portion in the arc of 20 cm in diameter corresponds to bending required to insert the insertion member 10 of the endoscope 2 into the intestinum cecum without a warp.

As mentioned above, among the components of the flexible tube that is a soft section, the hardness exhibited by the metallic members is made higher than the hardness exhibited by the nonmetallic members. In other words, the flexibility of the flexible tube that is a property thereof is determined based mainly on the hardness exhibited by the metallic members whose properties are unsusceptible to high-pressure steam. Consequently, deterioration of the properties of the flexible tube derived from repeated sterilization with high-pressure steam can be prevented reliably.

The constituent feature of the present embodiment would be effectively implemented in even the flexible tube of an endoscope that is designed to be sterilized or disinfected according to any method other than high-pressure steam sterilization. When the present embodiment is adapted to an endoscope, deterioration of the properties of the soft section of the endoscope can be prevented reliably.

Moreover, the hardness of the flexible tube 15 may be different among the portions of the flexible tube 15 in consideration of inserting smoothness. Generally, when the hardness of the flexible tube 15 is made different among the portions thereof in order to optimize inserting smoothness, the proximal portion of the flexible tube 15 is made softer than the tip portion thereof. This is because deterioration of the properties of especially the tip portion must be prevented to the greatest possible extent. In this case, the hardness of at least the tip portion the flexible tube 15 is set so that the hardness exhibited by the metallic members of the flexible tube 15 will exceed 50% of the hardness of the flexible tube 15.

Figure 5:
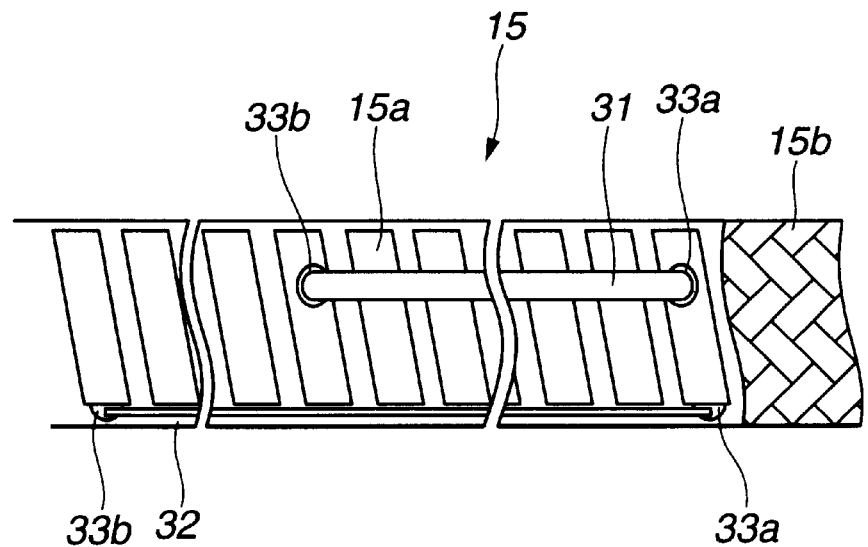
FIG. 5 is an explanatory diagram showing another structure of a flexible tube.

FIG. 5 is an explanatory diagram showing another structure of a flexible tube employed in a second embodiment of the present invention.

As shown in the figure, according to the present embodiment, two kinds of belt-like wires, that is, a first belt-like wire 31 and a second belt-like wire 32 that have different dimensions are interposed as flexibility adjustment metallic members between the braid 15b and spiral tube 15a in the flexible tube 15 instead of the stylet 23.

The belt-like wires 31 and 32 have, for example, a thickness of about 0.1 mm, a width of about 1 mm, and a length of, for example, 500 mm, 1000 mm, or more that corresponds to the length of the flexible tube 15 of the endoscope 2.

Both the ends of the belt-like wires 31 and 32 are firmly fixed to the spiral tube 15a or to hard members located near the spiral tube 15a by performing soldering or brazing. At this time, fixtures 33a to which the proximal ends of the belt-like wires 31 and 32 are fixed are located substantially at the same position in the proximal portion of the flexible tube 15. The positions of fixtures 33b to which the tip ends of the belt-like wires 31 and 32 are fixed are largely different from each other. Consequently, the hardness exhibited by the proximal portion of the flexible tube 15 is higher than the hardness exhibited by the tip portion thereof. This results in excellent inserting smoothness. The other components are identical to those of the first embodiment.

As mentioned above, the belt-like wires are interposed between the braid and spiral tube. Consequently, since the belt-like wires exhibit certain hardness and restrict bending of the spiral tube, desired flexibility can be attained. When the belt-like wires are placed in the flexible tube, the metallic members more greatly affect the flexibility of the flexible tube.

Moreover, since the belt-like wires are interposed between the spiral tube and braid, when the flexible tube is bent, the belt-like wires prevent compression of other built-in components.

Furthermore, since the belt-like wires are thin, the outer diameter of the endoscope will not increase but desired flexibility can be attained readily.

Figure 6:
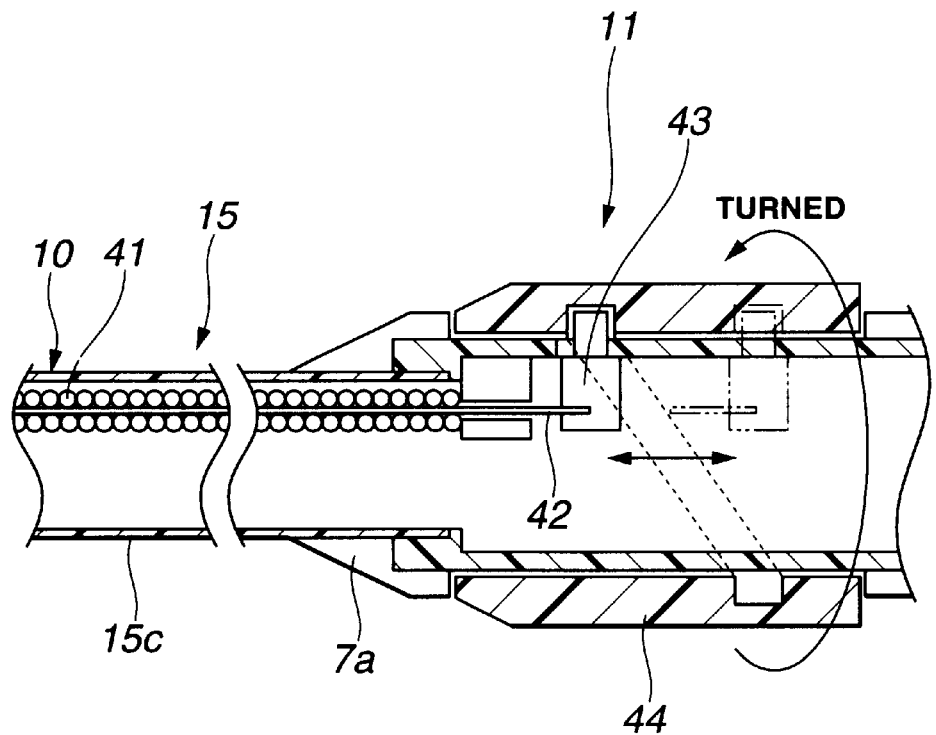
FIG. 6 is an explanatory diagram showing still another structure of the flexible tube.

FIG. 6 is an explanatory diagram showing another structure of a flexible tube employed in a third embodiment of the present invention.

As shown in the figure, according to the present embodiment, a hardness changing means for adjusting the hardness of the flexible tube 15 is included as a flexibility adjustment metallic member in the flexible tube 15 instead of the stylet 23 employed in the first embodiment or the belt-like wires 31 and 32 employed in the second embodiment.

The hardness changing means comprises a hardness change coil 41, a hardness change wire 42, a traction member 43, and a hardness change ring 44 used to adjust hardness. The hardness change coil 41 and hardness change wire 42 are metallic members made of, for example, stainless steel and passed through the insertion member 10. The traction member 43 is fixed to the proximal end of the hardness change wire 42. The hardness change ring 44 has a cam mechanism that changes the position of the traction member 43 in the longitudinal direction.

The tip end of the hardness change coil 41 is fixed to the hardness change wire 42. When the hardness change wire 42 lies as indicated with a solid line but is not pulled by the traction member 43, no extraneous force is applied to the hardness change coil 41. The hardness change coil 41 therefore remains soft.

When the hardness change ring 44 is turned, the traction member 43 moves from the position indicated with the solid line to a position indicated with an alternate long and two short dashes line. Compressive stress is gradually applied to the hardness change coil 41. Consequently, the hardness that discourages bending increases. When the traction member 43 reaches the position indicated with the alternate long and two short dashes line, the hardness is maximized.

According to the present embodiment, the hardness exhibited by the metallic members including the hardness change wire 42 and hardness change coil 41 exceeds 50% of the hardness of the flexible tube 15 with the hardness change coil 41 thereof set to the maximum hardness.

Consequently, if the properties of, for example, the sheathing tube 15c deteriorate because of repeated sterilization with high-pressure steam (or any other sterilization or disinfection), the flexible tube 15 may become softer than it initially is and have resiliency thereof deteriorated. In this case, the hardness of the hardness change coil 41 that is a nonmetallic member whose properties hardly deteriorate is changed in order to restore desired hardness and desired resiliency. The flexible tube can be reused.

Moreover, during examination, an operator turns the hardness change ring 44, so that the hardness of the flexible tube 15 can be controlled.

As mentioned above, the hardness changing means is used as a flexibility adjustment member. Even if the properties of the flexible tube deteriorate, desired hardness and desired resiliency can be restored repeatedly by changing the hardness of the hardness change coil.

Moreover, by properly changing the hardness of the hardness changeable flexible tube, a user can use the endoscope with a sense of desired hardness.

Even if a user likes the maximum hardness level within a range of hardness levels within which the hardness of the flexible tube can be varied, the hardness exhibited by the metallic members exceeds 50% of the hardness of the flexible tube 15 that is set to the maximum hardness level. The same operations and advantages as those mentioned above can be provided in terms of time-sequential deteriorations of hardness and resiliency.

Having described the preferred embodiments of the invention referring to the accompanying drawings, it is to be understood that the invention is not limited to those precise embodiments and that various changes and modifications thereof could be effected by one skilled in the art without departing from the spirit or scope of the invention as defined in the appended claims.

What is claimed is:

1. An endoscope having built-in components lying therethrough comprising:

an elongate flexible tube having a predetermined flexibility which is inserted into an object;

a metallic structure including elongate metallic members constituting the flexible tube;

a nonmetallic structure including elongate nonmetallic members constituting the flexible tube;

an elongate metallic tubular member included in the metallic structure; a plurality of metallic built-in slender components included in the metallic structure and lying through the flexible tube;

elongate nonmetallic tubular members included in the nonmetallic structure; and a plurality of nonmetallic built-in slender components included in the nonmetallic structure and lying through the flexible tube, wherein a desired force applied in the radial direction of the flexible tube required to bend the flexible tube by a predetermined amount is the sum of a force required to bend the metallic structure by the predetermined amount and a force required to bend the nonmetallic structure by the predetermined amount, and the force required to bend the metallic structure by the predetermined amount is set larger than the force required to bend the nonmetallic structure by the predetermined amount.

2. An endoscope according to claim 1, wherein the metallic structure including elongate metallic members constituting the flexible tube includes a flexibility adjustment metallic member that is intended to change a bending property of the flexible tube.

3. An endoscope according to claim 2, wherein the flexibility adjustment metallic member is a stylet made of a super-elastic alloy.

4. An endoscope according to claim 2, wherein the flexibility adjustment metallic member is a belt member placed along an armor in the longitudinal direction of the flexible tube.

5. An endoscope according to claim 2, wherein the flexibility adjustment metallic member serves as a level changing means for changing the level of the force required to bend the metallic structure by the predetermined amount; and the force level of the flexible tube is determined with the force level changing means set to the maximum force level so that the force required to bend the metallic structure by the predetermined amount is set larger than the force required to bend the nonmetallic structure by the predetermined amount.

6. An endoscope capable of being sterilized with high-temperature high-pressure steam comprising:

a flexible tube having a predetermined flexibility which is inserted into an object;

a metallic structure including elongate metallic members constituting the flexible tube and having a bending property which hardly change in the high-temperature high-pressure steam;

a nonmetallic structure including elongate nonmetallic members constituting the flexible tube and having a bending property which easily changes in the high-temperature high-pressure steam;

elongate metallic tubular members included in the metallic structure;

a plurality of metallic built-in slender components included in the metallic structure and lying through the flexible tube;

an elongate nonmetallic tubular member included in the nonmetallic structure; and a plurality of nonmetallic built-in slender components included in the nonmetallic structure and lying through the flexible tube, wherein a desired force applied in the radial direction of the flexible tube required to bend the flexible tube by a predetermined amount is the sum of a force required to bend the metallic structure by the predetermined amount and a force required to bend the nonmetallic structure by the predetermined amount, and the force required to bend the metallic structure by the predetermined amount is set larger than the force required to bend the nonmetallic structure by the predetermined amount, after the flexible tube is subjected to the high-temperature high-pressure steam.

7. An endoscope according to claim 6, wherein the metallic structure including elongate metallic members constituting the flexible tube include a flexibility adjustment metallic member that is intended to change a bending property of the flexible tube.

8. An endoscope according to claim 7, wherein the flexibility adjustment metallic member is a stylet made of a super-elastic alloy.

9. An endoscope according to claim 7, wherein the flexibility adjustment metallic member is a belt member placed along an armor in the longitudinal direction of the flexible tube.

10. An endoscope according to claim 7, wherein the flexibility adjustment metallic member serves as a level changing means for changing the level of the force required to bend the metallic structure by the predetermined amount; and the force level of the flexible tube is determined with the force level changing means set to the maximum force level so that the force required to bend the metallic structure by the predetermined amount is set larger than the force required to bend the nonmetallic structure by the predetermined amount.

* * * * *